United States Patent
Angal et al.

(10) Patent No.: US 7,105,834 B2
(45) Date of Patent: Sep. 12, 2006

(54) FLUORESCENT COATING VOID DETECTION SYSTEM AND METHOD

(75) Inventors: Jayant R. Angal, Louisville, KY (US); Paul D. Gossen, Louisville, KY (US); Stephen W. Brewer, New Albany, IN (US)

(73) Assignee: Innovative Productivity, Inc., Loiusville, KY (US)

( * ) Notice: Subject to any disclaimer, the term of this patent is extended or adjusted under 35 U.S.C. 154(b) by 0 days.

(21) Appl. No.: 11/040,143

(22) Filed: Jan. 21, 2005

(65) Prior Publication Data

US 2006/0163491 A1    Jul. 27, 2006

(51) Int. Cl.
G01N 21/64    (2006.01)

(52) U.S. Cl. .............. 250/458.1; 356/237.5; 356/237.1; 356/237.4; 438/16

(58) Field of Classification Search ............. None
See application file for complete search history.

(56) References Cited

U.S. PATENT DOCUMENTS

| | | | |
|---|---|---|---|
| 4,692,690 A | 9/1987 | Hara et al. | |
| 4,922,113 A | 5/1990 | Melancon | |
| 4,978,731 A | 12/1990 | Melancon et al. | |
| 5,493,123 A | 2/1996 | Knollenberg et al. | |
| 5,532,817 A * | 7/1996 | DeVries et al. | 356/318 |
| 6,501,075 B1 | 12/2002 | Trigiani | |
| 6,768,510 B1 * | 7/2004 | Ia Grone et al. | 348/223.1 |
| 6,809,809 B1 * | 10/2004 | Kinney et al. | 356/237.5 |
| 2002/0053589 A1 | 5/2002 | Owen et al. | |
| 2002/0135758 A1 | 9/2002 | Potyrailo et al. | |
| 2003/0160182 A1 | 8/2003 | Petrich et al. | |

FOREIGN PATENT DOCUMENTS

| | | |
|---|---|---|
| JP | 03075546 | 3/1991 |
| JP | 03229109 | 10/1991 |
| JP | 05340880 | 6/1992 |
| JP | 06215995 | 8/1994 |
| JP | 11352013 | 12/1999 |
| JP | 2000221146 | 8/2000 |

OTHER PUBLICATIONS

"Standard Recommended Practice Discontinuity (Holiday) Testing of New Protective Coatings on Conductive Substrates," NACE International, The Corrosion Society; Nace Standard RP0188-99, Item No. 21038, pp. 1-5, Revised Jan. 15, 1999, (c)1999, NACE International, Houston, Texas, U.S.A.

* cited by examiner

Primary Examiner—Nikita Wells
Assistant Examiner—Zia R. Hashmi
(74) Attorney, Agent, or Firm—Alexander P. Brackett; Middleton Reutlinger

(57) ABSTRACT

A system for detecting voids or imperfections such as holidays in a coating having fluorescent material therein comprises a camera having a digital image output for inspecting the coating wherein said camera's digital image output may include only the image produced by light in a color spectrum corresponding to a portion of the spectrum of light produced by fluorescent emission of the coating, thereby revealing the presence of any imperfections. Furthermore, an ultraviolet light source is provided to illuminate the coating and excite fluorescent emission therein. In one embodiment, the system is capable of distinguishing between an imperfection and the complete absence of a substrate surface. The system is also capable of revealing coating defects or imperfections in irregular surfaces. A microcontroller is also provided, having an associated memory, an input for accepting the digital image output from the camera, and an output representative of an analyzed digital image wherein said analyzed digital image includes visible indicia of any voids or imperfections detected in the coating.

31 Claims, 4 Drawing Sheets

FLUORESCENT COATING VOID DETECTION SYSTEM AND METHOD

STATEMENT REGARDING FEDERALLY SPONSORED RESEARCH

This invention was made with Government support under contract number N63394-02-C-4014 awarded by the Department of Defense. The Government has certain rights in the invention.

FIELD OF THE INVENTION

The present invention relates generally to a system and method for conducting inspections of coated components and specifically to a system and method for detecting imperfections, discontinuities, voids, or "holidays" in coatings containing fluorescent pigments therein. One application for which the present invention is well suited is for the detection of holidays in coatings on components having irregular surface shapes. Those skilled in the art will perceive many other applications of the present invention.

For purposes of the present disclosure the terms "void," "holiday," and "discontinuity" are used interchangeably and are taken to mean any void, crack, thin spot, foreign material inclusion or contamination in a coating that exposes any unprotected surface to the environment, or an area of coating that only minimally protects said surface, such as thin spots or bubbles that do not necessarily expose any unprotected surfaces to the environment, but are nonetheless recognized as flows in a coating.

BACKGROUND OF THE INVENTION

It is a known phenomenon that certain fluorescent materials are capable of absorbing radiated electromagnetic energy in the near ultraviolet spectrum and emitting it at a longer wavelength in the visible spectrum of light. This phenomenon enables various inspection and detection techniques using fluorescent dyes or pigments illuminated by an ultraviolet radiation source that then re-radiate with luminescence in the visible spectrum. For example, a refrigerant soluble fluorescent dye is often used in air conditioning systems to detect slow leaks therein. The fluorescent dye glows at a leak site when bathed in UV light.

Similarly, many paints and coatings may employ fluorescent agents therein to permit the coatings to be inspected once applied to a surface or substrate simply by exposing the coated surface to a UV light source and carefully examining the light pattern emitted therefrom. This technique is often employed where maximal coating integrity over a surface is necessary. For example in naval applications wherein coated components are routinely subjected to salt water and its corrosive effects, it is typically useful to conduct a thorough inspection of all coated components to detect the presence of any voids, imperfections or "holidays" in the applied coating, thereby permitting corrective action prior to placing the component in service.

However, since fluorescence is a fairly weak effect, high intensity UV light sources are required for accurate and reliable holiday detection. Additionally, many areas that must be coated, such as ballast tanks on ships, are not readily accessible or visible and thus are not amenable to a simple process of UV light irradiation and attendant visual inspection. Furthermore, many coated areas requiring inspection have irregular surfaces that require more thorough scrutiny to determine the absence or presence of holidays in the coating. This problem is particularly acute in welded areas that are coated, since the surfaces of weld beads tend to be highly irregular and thus prove difficult to thoroughly coat and inspect. Discontinuities in coatings are often quite small and as such, are not readily visible to the naked eye.

Prior art coating inspection techniques have proven to be unwieldy and inefficient. For example, a wet sponge/conductivity test is often employed wherein a voltage is applied to a wet sponge which is them slowly moved over the entire surface. This test may only be employed where a non-conductive coating is applied to a conductive surface. Where a void or holiday is present, an electrical current will flow through the sponge as electricity is conducted from the void area through the wet sponge. Many wet-sponge testing systems employ other visual or audible indicators to alert an inspector to a coating discontinuity. This holiday detection technique is both time and labor intensive, since the sponge must be moved over the entire coated surface in order to detect any holidays. Furthermore, this inspection technique can only be used be when the coating being inspected is completely cured, thereby delaying inspection of freshly applied coatings.

Some camera-based inspection systems do exist, but these systems suffer from an inability to operate in low-light conditions and often prove slow to operate. Furthermore, prior art systems are costly, bulky and unwieldy, and are unable to discriminate between an absence of fluorescence caused by a void and the complete absence of a surface. Another particular difficulty with prior art inspection systems is the inability to inspect portions of surfaces due to the effects of glare and shadows caused by illumination or incident light.

SUMMARY OF THE INVENTION

The present invention obviates the aforementioned problems by providing a readily portable system and method for inspecting voids in coatings containing fluorescent pigments, employing a plurality of light sources for exciting the fluorescent coatings and a camera having a digital image output for detecting the voids in said coatings based upon the type of light emitted and reflected therefrom. The camera may be provided as a component of a sensor head that may include a plurality of ultraviolet light sources and/or a plurality of red light sources. These light sources may preferably be arrayed around a lens of said camera to flood the area being viewed with light from a plurality of incident angles thereby reducing glare from the perspective of the camera lens.

Additionally a filter may also be employed in conjunction with the UV light array to select the UV light frequencies to the specific excitation frequencies desired for excitation of the selected fluorescent coatings, as well as prevent the camera lens from picking up broad spectrum UV light reflected back from the surface being inspected, which is essentially unwanted light for purposes of the present invention.

Furthermore, an analyzer module including a conventional microcontroller may be provided that is electrically connected to the camera to accept a plurality of digital images therefrom and analyze them to determine whether any holidays are revealed by the character of the light reflected from the surface being inspected. The analyzer module may incorporate a digital image output that is subsequently supplied to a display to permit an operator to view an image of the surface being inspected wherein the image may include a highlighted or flashing portion indicative of a detected holiday.

Additionally, the present invention may include an audible alarm for alerting an operator to a holiday detection event, as well as a power source such as a battery, or a plurality thereof, to enhance portability of the invention.

Other features and objects of the present invention will become apparent from the detailed description of the preferred embodiment(s) as well as the drawing Figures included herein below.

BRIEF DESCRIPTION OF THE DRAWING FIGURES

DETAILED DESCRIPTION OF THE PREFERRED EMBODIMENT(S)

Figure 1:
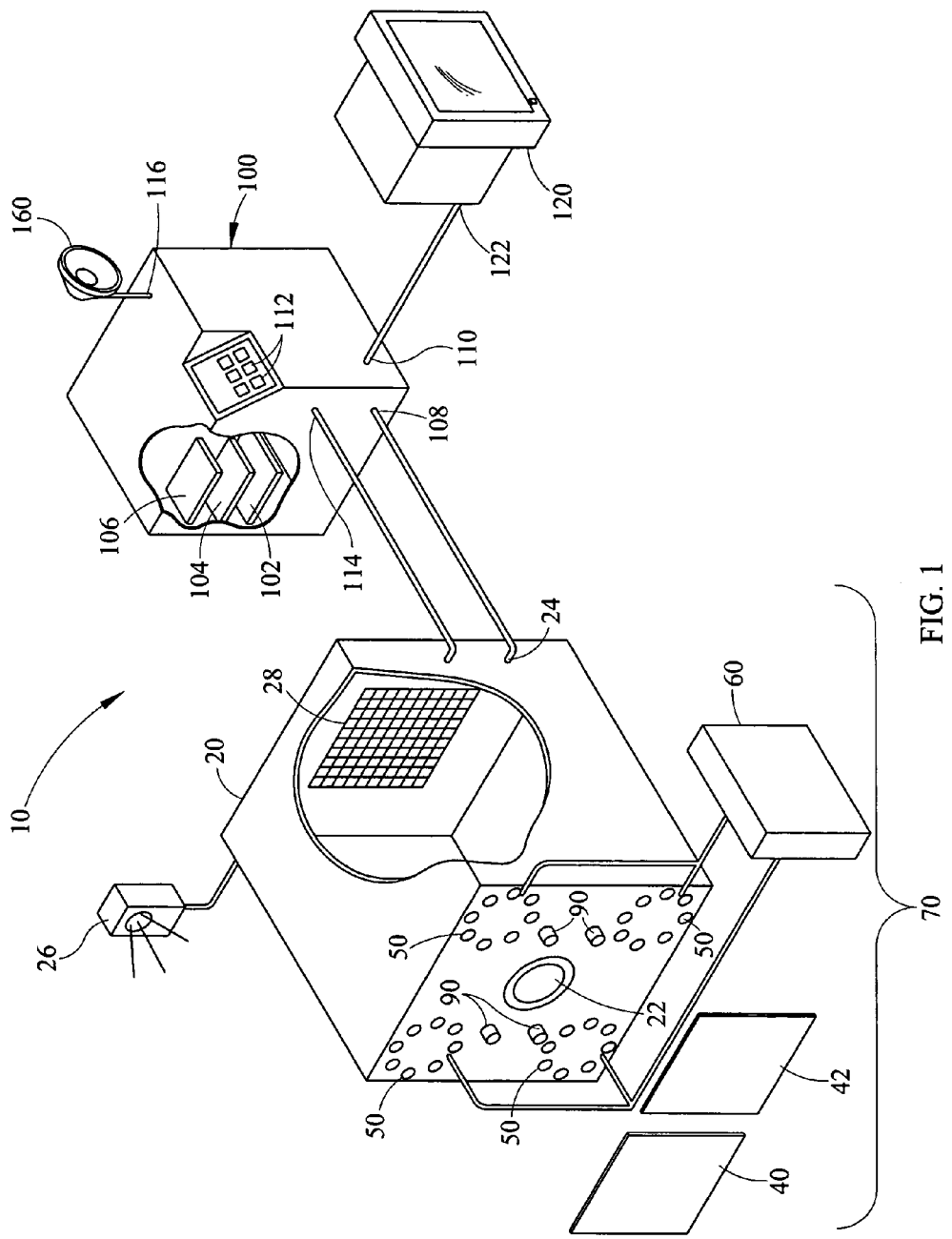
FIG. 1 is a schematic diagram in accordance with one embodiment of the present invention.

Referring now to the drawing Figures, and in accordance with a constructed embodiment of the present invention, a system 10 and method for detecting voids in coatings 1 containing fluorescent materials includes a camera 20 having a lens 22 and a digital output 24 that is representative of an image as seen through the lens 22 of the camera 20. The camera 20 may include an integral or detached flash 26 that emits light synchronously with the operation of a shutter (or image acquisition mechanism) of the camera 20, as is well known in the art. While a variety of cameras may be advantageously employed in the system of the present invention, in one embodiment the camera lens 22 has a sixty degree cone angle that is focus optimized for 100 millimeters and has a depth of field sufficient to obtain clear images from 50 millimeters to infinity. A camera 20 having these specifications permits an operator to procure clear images of the coated surfaces being inspected without the necessity of operating a focus ring, f-stop, or other camera control. In one embodiment of the invention, the camera 20 is capable of capturing images at a rate of 30 frames per second (fps), while in another embodiment of the present invention a video camera 20 may be employed.

Furthermore, an alternative embodiment of the present invention includes a first optical filter 40 disposed over the lens 22 of the camera 20 thereof such that any light entering the lens 22 must first pass through the first optical filter 40. The first optical filter 40 is selected to block those wavelengths of light that include the wavelengths that excite the fluorescence of the coating(s) 1 being inspected. Thus the camera 20 obtains an image that includes the light emitted through the effect of fluorescence but devoid of details from the spectrum of light rejected by the first optical filter 40. One of ordinary skill in the art will recognize that the placement of the first optical filter 40, whether in front of or behind the lens 22 of the camera 20, does not affect the operation of the present invention. In a further embodiment of the invention, a second optical filter or filters 42 may be disposed over the light source(s) required to provide excitation radiation to the fluorescent coating 1, thereby limiting the spectrum of light reaching the target surface 2 and reducing undesirable glare, as will be discussed in greater detail herein below.

Accordingly, voids in the coated surface 2 will appear as dark spots (pixels) on the digital image taken by the camera 20, since little or no light in the fluorescent wavelength will be emitted from the section of the surface representative of a coating void. Accordingly, the present invention is particularly suited for detecting voids in fluorescent coated surfaces, even where those voids may be undetectable to the naked eye.

In one embodiment of the present invention a camera 20 employing an image sensor 28 utilizing a CCD (charge-coupled device) semiconductor chip with a color mask to produce the digital image output may be used. The CCD image sensor 28 enables the camera 20 to "look" for (detect) light impinging on the sensor 28 at a predetermined wavelength or range of wavelengths, depending upon the use of a selected color filter, typically corresponding to a color range including the wavelength of fluorescent emission from a specified fluorescent coating. This feature of the present invention permits the invention to be operated without the necessity of using a separate optical filter, since the image sensor 28 is capable of color-masking to only view a specified color light. Cameras incorporating sensors with CCD technology are available from a wide variety of commercial sources. In one embodiment of the invention a pinhole lens 22 color camera 20 capable of capturing images at 30 frames per second (fps) is employed, and is available from, for example Point Grey Research Incorporated.

While one embodiment of the present invention employs a camera 20 utilizing a CCD image sensor 28, one of ordinary skill in the art will appreciate that a wide variety of cameras may be used in the system 10. Types of cameras 20 that may be employed include, but are not limited to one-chip one-shot cameras, one chip three shot cameras, two and three chip cameras, and cameras employing both area array and linear image sensors. Furthermore, the image sensors 28 used in the aforementioned cameras are not limited to CCD sensors, but may also include CMOS (complementary metal oxide semiconductor) sensors or other digital image sensors.

Additionally, the present invention may incorporate an ultraviolet (UV) light source 50, or alternatively a plurality thereof, disposed in an array around the lens 22 of the camera 20 in order to provide comprehensive UV light illumination of the inspection target at a plurality of incident angles. This feature of the invention aids in the reduction of glare seen by the camera 20. The UV light sources 50 may comprise a plurality of UV light emitting diodes (LEDs) emitting light at a wavelength sufficient to excite fluorescent emission in the coating 1 being inspected. Many known-in-the-art fluorescent coatings fluoresce responsive to radiation in the indigo, violet or blue light spectrums, that is to say near to and below 420 nm wavelengths. Accordingly, as one example, the present invention may incorporate a second optical filter 42 disposed between the UV LEDs and the inspection target that only permits passage of light having wavelengths between approximately 300 and 409 nm to provide targeted excitation radiation to the fluorescent coatings 1. One of ordinary skill in the art will understand that the second optical filter 42 can be selected to pass those frequencies of light required for excitation of a given fluorescent coating. Alternatively, in accordance with one embodiment of the present invention, the LEDs used to illuminate the target coating 1 may be selected to emit radiation in the spectrum required to excite fluorescent emission for a given coating 1. Accordingly, it is possible to either select an appropriate second optical filter 42 to tailor the excitation light spectrum based on a UV LED array 50, or select an LED array to correspond to the requisite excitation light spectrum.

In a yet further embodiment of the present invention the UV LEDs may be energized to emit light synchronously with the operation of the camera 20 in order to reduce the requisite electrical power required to operate the UV LEDs as well as extend the useful life of the LEDs. This may be accomplished by utilizing a commercial strobe controller 60 to deliver a limited current pulse to the LED array synchronously with the camera 20 image acquisition operation. For purposes of this specification, the terms shutter operation, image acquisition, and data collection may be used interchangeably to denote the act of taking a digital picture or image. One embodiment of the invention uses a 24VDC strobe controller 60 available from Advanced Illumination Corporation to deliver a strobed current pulse to the UV LED array, synchronized with the operation of the camera 20 shutter. Since the UV LEDs are operating on a partial duty cycle, they operate at a cooler temperature thus extending the useful life of the LED array.

Figure 4:
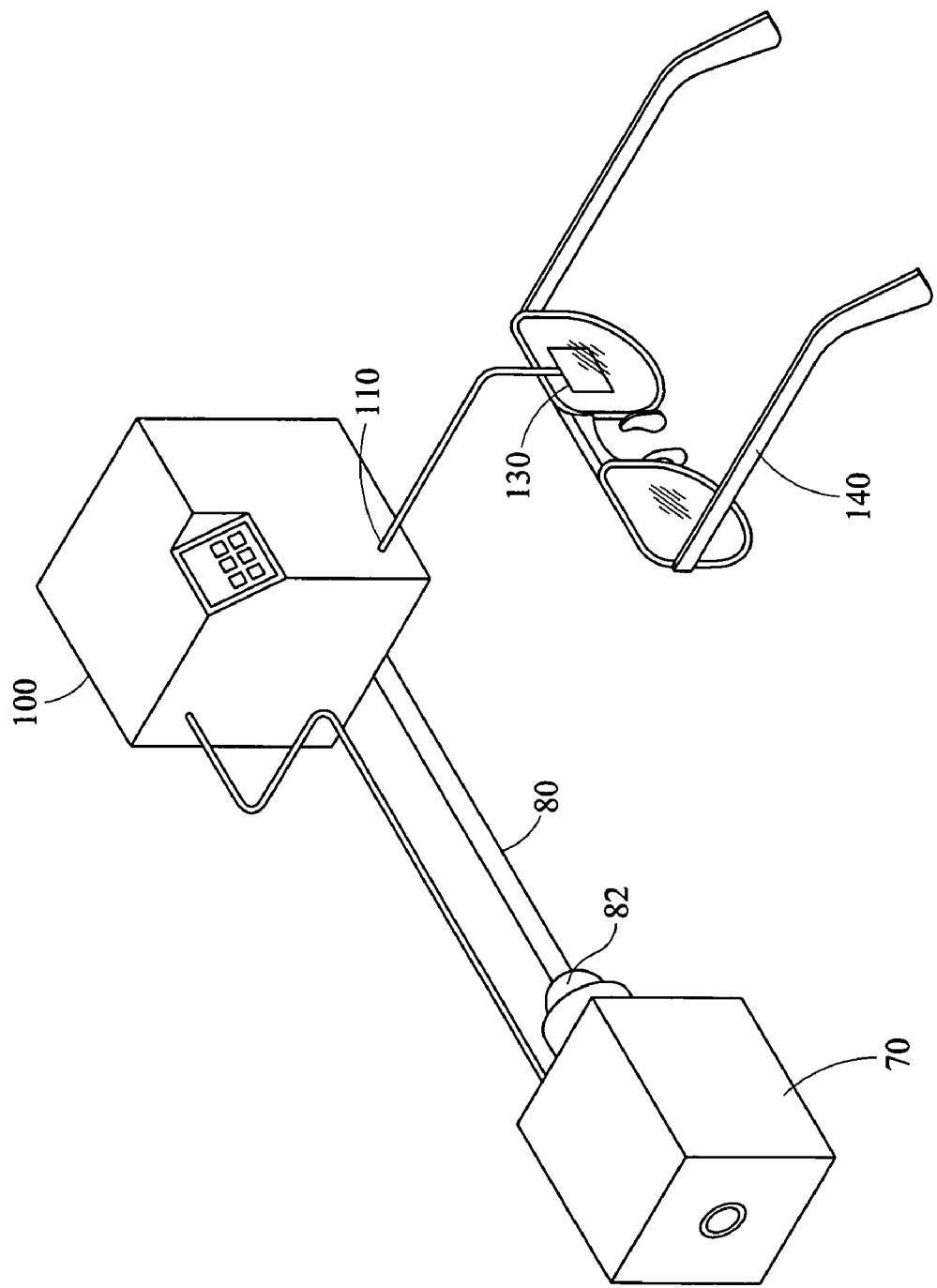
FIG. 4 is a schematic diagram in accordance with one embodiment of the present invention.

Note that the camera 20, first and second optical filters 40 and 42, LED illumination array 50, and strobe controller 60 may be integrated into a single sensor head 70 unit. As seen in FIG. 4, this sensor head 70 may then be located at the end of a wand 80 and mounted on a swivel 82 or other articulated joint, so that an operator may readily direct the sensor head 80 to a surface being inspected that may be difficult to reach or view by line-of-sight. This feature of the invention permits it to be advantageously operated to inspect coatings 1 in a wide variety of industrial applications wherein surfaces 2 having complex surface geometries must be coated and inspected. Alternatively, the sensor head 50 may be used as a hand held unit for ease of inspection of surfaces in tighter areas where a wand 80 may prove unwieldy.

In an alternative embodiment of the present invention an array of LED's 90 capable of light emission in the red wavelength spectrum is disposed around the lens 22 of the camera 20 to provide red light illumination of the coating 1 being inspected. In one embodiment of the invention, the red LED array 90 emits light having a peak wavelength of 660 nm, ±5 nm. The red light LED array 90 is not subject to filtration by the second optical filter 42, where used. This feature of the present invention permits an operator to use the red light in a "flashlight" mode where the red LED's 90 are simply used to illuminate the target surface 2, and furthermore to detect the absence of a surface 2 being inspected, as will be discussed in greater detail herein below.

The present invention further comprises an analyzer module 100 comprising a microcontroller 102 having a processor 104 and an associated memory 106 for storing and manipulating image data. The microcontroller 102 further includes an input 108 capable of accepting the digital image output 24 of the camera 20 and an output 110 representative of a manipulated or analyzed image depicting the surface 1 being inspected as well as any holidays detected therein.

The microcontroller 102 produces this manipulated image by examining the digital image input 24 supplied by the camera 20 and executing a detection algorithm thereon. The algorithm may be executed by supplying the microcontroller 102 processor 104 with suitable software programming instructions representative of the algorithm steps. In one embodiment of the present invention, the processor 104 is supplied with programming instructions written using the C++ programming language, but one of ordinary skill in the art will appreciate that one of many commercially available programming languages may be employed in the system 10 and method of the present invention.

Figure 2:
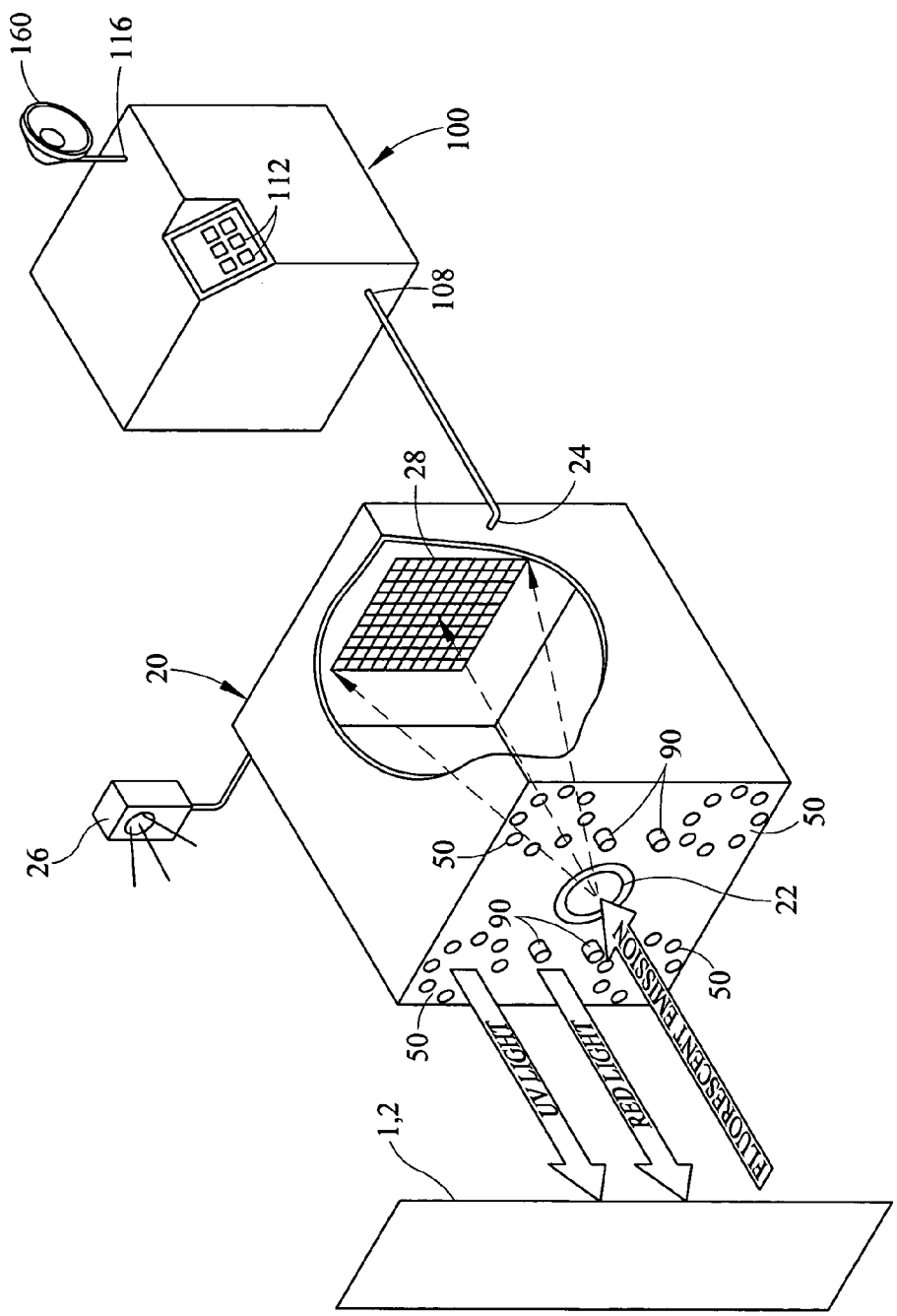
FIG. 2 is a schematic diagram in accordance with one embodiment of the present invention.
Figure 3:
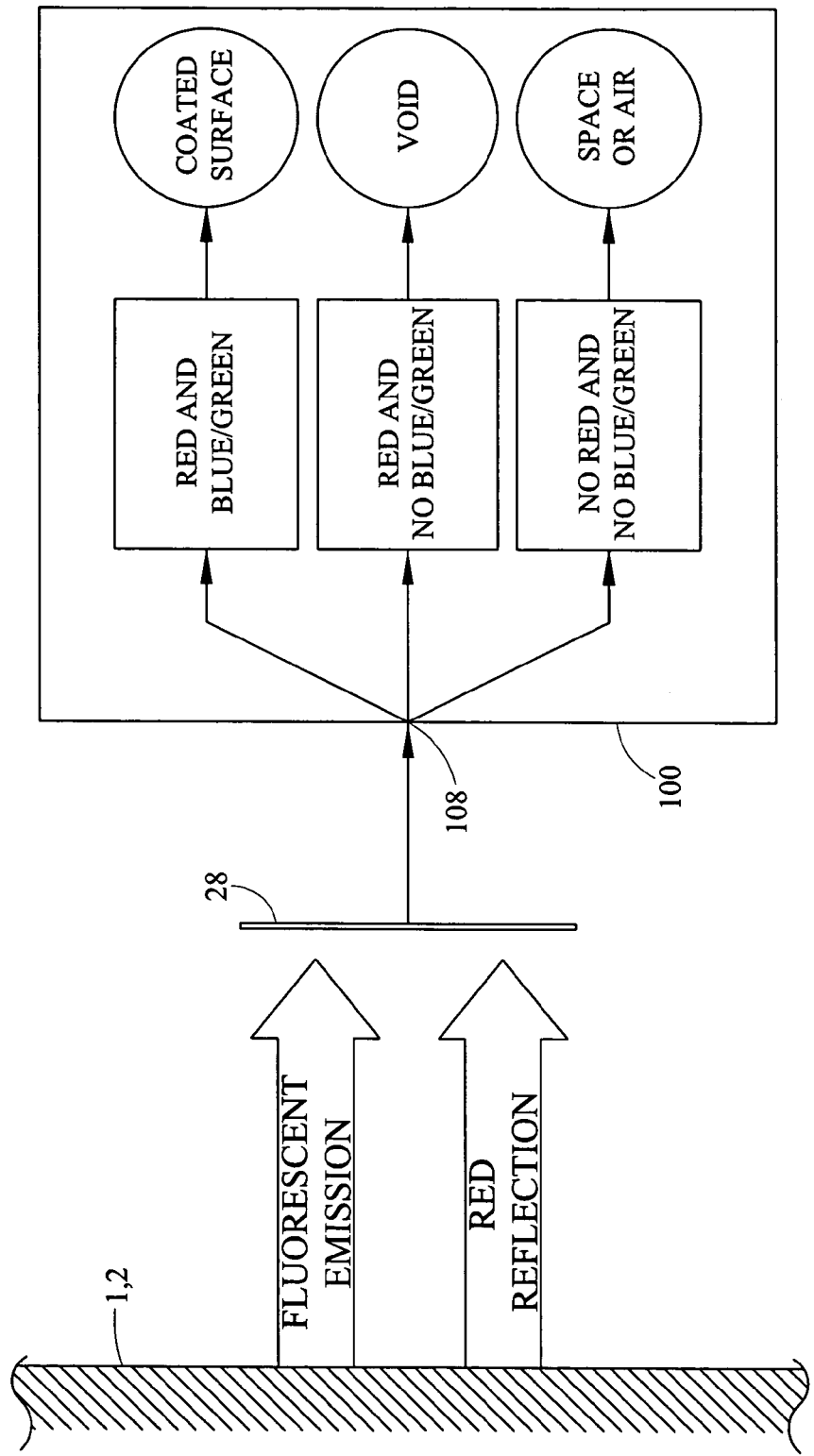
FIG. 3 is a schematic diagram in accordance with one embodiment of the present invention.

An algorithm used to detect voids or holidays simply examines the digital image stored by the camera 20 to determine the absence of light in the fluorescent emission spectrum for the specific coating 1 being inspected. Referring to drawing FIGS. 2 and 3 as an instructive example, many known-in-the-art fluorescent coatings emit radiation in the blue to green light spectrum. Where an imperfection or void is present in the coating, little or no light will be emitted from that portion thereof and therefore the imperfection or void will appear as a reduction of, or complete absence of fluorescent emission on the image. Thus the algorithm simply examines the image pixel by pixel to determine where the blue to green color present in the image is below a predetermined threshold, and marks those portions of the image as holidays. In one embodiment of the present invention the analyzer 100 "flags" the holidays present in an image by outlining the portions of the image representative of a void with a contrasting color for viewing on a display 120. Furthermore, the contrasting color outline may be programmed to flash on and off when the analyzed image is displayed, thereby providing enhanced visual indicia of the presence of a holiday. In a yet further embodiment of the present invention, where the analyzer 100 detects a holiday, the analyzer 100 flags the holiday in the digital image.

Referring again to FIGS. 2 and 3, in the embodiment of the present invention wherein red LED illumination is also used, the detection algorithm processed by the analyzer 100 may be adapted to permit the invention 10 to detect the absence of a surface 2 being inspected so that a false positive (void detection) is not generated when the image, or a portion thereof, simply contains blank space. In this embodiment of the present invention, the analyzer 100 looks at light from the image in both the blue to green spectrum and the red spectrum. Since light in the red spectrum is simply reflected back from the target surface 2, whether coated or not, any portion of the image that does not include light in the red wavelength spectrum is simply air or blank space. In other words, where no red light exists in the image, no surface 2 is present. Thus those portions of the image that include both red and blue to green light are properly coated surfaces. In contradistinction, those portions of the image that include red light and exclude light produced by fluorescent emission are holidays in the coated surface 2. As can be readily seen, this feature permits the present invention to discriminate between a false void detection and the absence of a coated surface 2, thereby providing great ease of use for an operator.

It should be noted that a wide variety of fluorescent coatings are available, capable of accepting many different spectrums of excitation light, and producing many different spectrums of fluorescent emission. For example, some fluorescent coatings accept green light for excitation, and emit light in the red spectrum responsive thereto. In this system, the camera 20 image sensor 28 is simply used to detect emitted light in the red spectrum. Where such a coating is used, it may be desirable to use light in the blue spectrum to illuminate the entire surface, so that the absence of blue light being reflected back to the camera 20 is indicative of the absence of a surface 2. Accordingly, in accordance with one embodiment of the present invention, the target coating 1 is illuminated by light in a first wavelength spectrum that includes the excitation frequency of the coating 1, and then emits light in a second wavelength spectrum, exclusive of the first, that is detected by the camera 20. Furthermore, the coating 1 may be illuminated by light in a third wavelength spectrum that is exclusive of the first and second spectra above, wherein the light in the third wavelength spectrum is detectable by the camera 20, and wherein its absence indicates the absence of a surface 2.

In one embodiment of the present invention, the analyzer 100 microcontroller 102 further includes a digital image output 110 that is connected to an input 122 of a visual display 120 to enable an operator to readily ascertain the presence of an outlined holiday in the coating 1. While a wide variety of commercially available displays 120 may be employed with the system and method of the present invention, including conventional video monitors, in one embodiment of the present invention, the display 120 employed is a heads-up viewer 130 capable of being mounted on the lens of safety eyewear or goggles 140. This embodiment of the present invention allows an operator working in an industrial environment to view the holiday detection image without moving to a remote location to view a monitor, and without the need to carry a miniaturized monitor. Furthermore, the ability to mount the viewer 130 on goggles 140 permits one-hand operation, thereby leaving the operator's other hand free to reach for handholds and safety railings necessary to navigate many industrial environments. This enables the inspection of coatings 1 for holidays to be undertaken by a single person, since only one hand is required to scan the coated surface with the camera 20 and UV light array 50. A suitable heads up display 130 for use in the system of the invention may be procured from, for example, the Micro Optical Corporation of Westwood, Mass.

The analyzer 100 may further include a plurality of operator inputs 112, for example sealed pushbuttons, to permit an operator to select various modes of operation as well as turn power on and off to the system. A power on/off pushbutton as well as a mode pushbutton may be provided. The mode pushbutton may be depressed a plurality of times to cycle through the various modes of operation permitted. Furthermore, the analyzer 100 may also include a communications output 114 electrically connected to an input of the sensor module, to convey mode operation information thereto.

Modes of operation of the present invention include a flashlight mode wherein the red LEDs 90 are used for surface 2 illumination but no coating 1 inspection is conducted, a camera 20 inspection mode without red LED illumination, a camera 20 inspection mode with red LED illumination, a holiday detection mode of fluorescent coating over non-fluorescent substrate, a holiday detection mode of nonfluorescent coating over fluorescent substrate, and a calibration mode.

In an alternative embodiment of the present invention, the microcontroller 102 further includes an output 116 connected to an audible alarm 160 capable of being heard by an operator. The alarm 160 may comprise a horn, buzzer, or other device capable of broadcasting sound at a decibel level sufficient to be heard by an operator in an industrial environment. The output 116 is activated (and thus the alarm is sounded) responsive to the detection of a holiday in the coating 1. This feature of the invention provides an additional indication of a holiday that will serve to focus the operator's attention on the portion of the coated surface 2 being inspected.

In a yet further embodiment of the instant invention the analyzer 100 may be mounted at a wand 80 end opposite the sensor head 70, analogous to a conventional metal detector. This feature allows an operator to direct the sensor head 70 as needed for surface coating 1 inspection while keeping the controls accessible to the operator. This feature also permits one-handed operation of the present invention.

In a yet further embodiment of the present invention, all communications between the analyzer and the sensor module may be accomplished through use of wireless communications, including the digital image output from the camera 20 to the analyzer. For example, many known-in-the art cameras are capable of radio transmission of video between the camera and a monitor.

In an alternative embodiment of the present invention, the camera image taken of the surface 2 being inspected utilizes only the green light pixels from a color sensor camera 20 for holiday detection. In this embodiment of the invention a green filter is used (typically internal to the camera) to obtain only the green light portions of the image impinging on the image sensor 28. In state of the art three-chip cameras a separate dedicated green image sensor 28 may be used wherein the photosites on the surface of the image sensor 28 are coated or covered with a green filter. Where a one-chip camera 20 is employed with a color mask filter (having a red/green/blue filter mask over the image sensor 28), one exposure captures the entire color pattern from the image sensor 28 and software is used to reconstruct separate blue, green and red images therefrom. In this case, only the green image exposure will be sent to the microcontroller 102 for analysis.

Since many known-in-the art fluorescent coatings emit light containing a portion of light from the green range of the light spectrum, by examining only the green portion of the image, which is just a portion of the spectrum of light produced by fluorescent emission, the analyzer 100 may readily ascertain the presence of a holiday on the surface, since the holiday will still appear as a dark pixel or pixels on the green image. This embodiment of the invention obviates the need for the use of costly optical filters for the UV LED array, since any unwanted UV light reflected back to the camera lens 22 is "ignored" by simply viewing the green color portion of the image. One of ordinary skill in the art will appreciate that the use of a green color mask as discussed herein above may be practiced using a variety of different imaging methods depending upon the design of the camera 20 being used. For example, in a camera 20 employing three chips (image sensors 28) the requisite image may be obtained by simply retrieving the image data from the chip corresponding to the green filter. Additionally, this embodiment of the present invention may readily be practiced with cameras 20 using alternative image sensors 28, for example CMOS sensors or direct image sensors.

The foregoing detailed description of the embodiments of the invention is presented primarily for clearness of understanding and no unnecessary limitations are to be understood or implied therefrom. Modifications to the present invention in its various embodiments will become obvious to those skilled in the art upon reading this disclosure and may be made without departing from scope of the invention encompassed by the claims appended hereto.

We claim:

1. A system for detecting imperfections in a coating having fluorescent material therein applied to a substrate comprising:

a camera having a lens and a digital image output for inspecting said coating wherein said camera's digital image output includes only the image produced by light in a color spectrum corresponding to a portion of the spectrum of light produced by fluorescent emission of said coating;

a first light source to illuminate said coating and excite fluorescent emission therein; and a microcontroller having an associated memory, an input for accepting the digital image output from said camera, and an output representative of an analyzed digital image wherein said analyzed digital image includes visible indicia of any imperfections detected in said coating.

2. A system as claimed in claim 1 wherein said light source comprises an array of light emitting diodes.

3. A system as claimed in claim 2 wherein said array of light emitting diodes is disposed around the lens of said camera.

4. A system as claimed in claim 1 further comprising a strobe controller capable of energizing said light source in synchronous operation with the image acquisition of said camera.

5. A system as claimed in claim 2 wherein said array of light emitting diodes is powered on synchronously with the image acquisition of said camera.

6. A system as claimed in claim 1 further comprising a second light source in a spectrum exclusive of said first light source, wherein said camera's digital image output further includes the image produced by light in the second color spectrum.

7. A system as claimed in claim 6 wherein said second light source comprises a second array of light emitting diodes to illuminate said coatings.

8. A system as claimed in claim 7 wherein said second array of light emitting diodes is disposed around the lens of said camera.

9. A system as claimed in claim 1 further comprising a display having an input for receiving the image output of said microcontroller wherein the analyzed digital image output may be viewed on said display.

10. A system as claimed in claim 9 wherein said display is a heads-up display.

11. A system as claimed in claim 1 wherein said camera and said first light source comprise a sensor head disposed at a point distant from said microcontroller.

12. A system as claimed in claim 6 wherein said camera, said first light source and said second light source comprise a sensor head disposed at a point distant from said microcontroller.

13. A system as claimed in claim 1 wherein said imperfections are voids.

14. A system as claimed in claim 1 wherein said imperfections are holidays.

15. A system for detecting imperfections in coatings having fluorescent material therein comprising:
    a camera having a lens, an image sensor and a digital image output;
    a first light source to illuminate said coating and excite fluorescent emission therein;
    a first optical filter for restricting the wavelengths of light reflected from said coating back to the image sensor of said camera;
    a microcontroller having an associated memory, an input for accepting the digital image output from said camera image sensor, and an output representative of an analyzed digital image wherein said analyzed digital image includes visible indicia of any imperfections detected in said coating.

16. A system as claimed in claim 15 wherein said first light source comprises an array of light emitting diodes.

17. A system as claimed in claim 15 further comprising a strobe controller capable of energizing said light source in synchronous operation with the image acquisition of said camera.

18. A system as claimed in claim 16 wherein said array of light emitting diodes is powered on synchronously with the image acquisition of said camera.

19. A system as claimed in claim 15 further comprising a second light source in a spectrum exclusive of said first light source, wherein said camera's digital image output further includes the image produced by light in the second color spectrum.

20. A system as claimed in claim 19 wherein said second light source comprises a second array of light emitting diodes to illuminate said coatings.

21. A system as claimed in claim 15 further comprising a display having an input for receiving the image output of said microcontroller wherein the analyzed digital image output may be viewed on said display.

22. A system as claimed in claim 21 wherein said display is a heads-up display.

23. A system as claimed in claim 15 wherein said camera and said first light source comprise a sensor head disposed at a point distant from said microcontroller.

24. A system as claimed in claim 19 wherein said camera, said first light source and said second light source comprise a sensor head disposed at a point distant from said microcontroller.

25. A system as claimed in claim 15 further comprising an audible alarm responsive to an output from said microcontroller, wherein the output is turned on to indicate the detection of an imperfection.

26. A system as claimed in claim 15 wherein said imperfections are voids.

27. A system as claimed in claim 15 wherein said imperfections are holidays.

28. A method for detecting imperfections in a coating having fluorescent material therein on a substrate comprising the steps of:
    illuminating said coating with light in a first spectrum designed to excite light emission by said coating of light in a second spectrum;
    capturing an image of said coating representative of the second spectrum of light caused by fluorescent emission of said coating;
    analyzing said image from step b to determine pixels therein that do not include a predetermined level of light emission from said coating, said pixels being representative of imperfections in said coating; and
    providing said analyzed digital image with visible indicia of any imperfections detected in said coating.

29. A method for detecting imperfections in a coating having fluorescent material therein on a substrate as claimed in claim 28 further comprising outlining any imperfections in said digital image with a contrasting color.

30. A method for detecting imperfections in a coating having fluorescent material therein on a substrate as claimed in claim 28 further comprising the steps of:
    i. illuminating said coating with light in a third spectrum exclusive of the first and second light spectra; and
    ii. analyzing said image to determine the presence of light in the third spectrum, wherein the absence thereof is indicative of the absence of a target surface.

31. A method for detecting imperfections in a coating having fluorescent material therein on a substrate as claimed in claim 28 further comprising the steps of:
    capturing an image of said coating representative of the first spectrum of light caused by reflection from said substrate coating; and
    analyzing said image to determine the presence of light in the first spectrum, wherein the absence thereof is indicative of the absence of a target surface.

* * * * *